US011335451B2

(12) United States Patent
Thotta et al.

(10) Patent No.: US 11,335,451 B2
(45) Date of Patent: May 17, 2022

(54) METHOD AND SYSTEM FOR IMPROVING WELLBEING OF A PERSON USING A DIGITAL CHARACTER

(71) Applicant: Tata Consultancy Services Limited, Mumbai (IN)

(72) Inventors: Ashwanth Thotta, Pune (IN); Sandeep Athavale, Pune (IN)

(73) Assignee: TATA CONSULTANCY SERVICES LIMITED, Mumbai (IN)

(*) Notice: Subject to any disclaimer, the term of this patent is extended or adjusted under 35 U.S.C. 154(b) by 120 days.

(21) Appl. No.: 16/824,744

(22) Filed: Mar. 20, 2020

(65) Prior Publication Data

US 2020/0388373 A1 Dec. 10, 2020

(30) Foreign Application Priority Data

Jun. 4, 2019 (IN) .............................. 201921022109

(51) Int. Cl.
*G16H 20/70* (2018.01)
*G16H 50/30* (2018.01)
*G06T 13/40* (2011.01)

(52) U.S. Cl.
CPC ............ *G16H 20/70* (2018.01); *G06T 13/40* (2013.01); *G16H 50/30* (2018.01)

(58) Field of Classification Search
CPC ......... G16H 20/70; G16H 50/30; G06T 13/40
See application file for complete search history.

(56) References Cited

U.S. PATENT DOCUMENTS

| 6,554,679 B1 * | 4/2003 | Shackelford ............. A63H 3/28 446/268 |
| 2005/0021372 A1 | 1/2005 | Mikkelsen et al. |
| 2014/0125678 A1 * | 5/2014 | Wang ..................... A63F 13/80 345/473 |

(Continued)

FOREIGN PATENT DOCUMENTS

WO    WO 2007/095314 A2    8/2007

OTHER PUBLICATIONS

Kern, M.L. et al. (2015). "A multidimensional approach to measuring well-being in students: Application of the PERMA framework," *The Journal of Positive Psychology*, vol. 10, No. 3; pp. 262-271.

*Primary Examiner* — Christopher L Gilligan
*Assistant Examiner* — Chance L Smith
(74) *Attorney, Agent, or Firm* — Finnegan, Henderson, Farabow, Garrett & Dunner, LLP (57) ABSTRACT

Efforts have been made in the past to improve the wellbeing of a person. Various methods involve use of virtual pet character which can interact with the person. But these methods are mainly for entertainment purpose, people get bored quickly. Moreover, the present application doesn't take into the input of the present state of user. A method and system for improving wellbeing of person using a digital character such as virtual pet has been provided. The system maintains a wellbeing index for both the user and digital character. A set of activities are provided which is performed by the digital character and the user. Further, a response of the user is also captured depending on the current wellbeing index using a set of questionnaire. And a second set of activities are recommended based on the response to further improve the wellbeing index of the person.

11 Claims, 4 Drawing Sheets

(56) References Cited

U.S. PATENT DOCUMENTS

| | | | |
|---|---|---|---|
| 2014/0206444 A1* | 7/2014 | Lin | A63F 13/216 |
| | | | 463/31 |
| 2016/0063874 A1* | 3/2016 | Czerwinski | G06Q 10/107 |
| | | | 434/236 |
| 2019/0088159 A1* | 3/2019 | Minturn | A63F 13/46 |
| 2020/0253527 A1* | 8/2020 | Ellison | A61B 5/165 |

* cited by examiner

METHOD AND SYSTEM FOR IMPROVING WELLBEING OF A PERSON USING A DIGITAL CHARACTER

PRIORITY CLAIM

This U.S. patent application claims priority under 35 U.S.C. § 119 to: India Application No. 201921022109, filed on 4 Jun. 2019. The entire contents of the aforementioned application are incorporated herein by reference.

TECHNICAL FIELD

The embodiments herein generally relates to the field of improving wellbeing of a person. More particularly, but not specifically, the invention provides a method and system for improving wellbeing of a person using a digital pet character on an electronic device.

BACKGROUND

Wellbeing is related to the health and happiness of a human being. Various efforts have been taken in the past to maintain/improve the wellbeing of the person. It is well known that pets can play a positive role in both the physical and psychological health of older adults. It is also known that pet dogs can act as catalysts for human social interactions, and it has been suggested that this may enhance feelings of well-being.

With the development of portable electronic devices such as laptop and mobile phones, people have started spending more and more time on those. Several approaches have been taken to improve the wellbeing of the person using the portable electronic devices. One such approach is the use of a digital character such as virtual pets on the electronic device.

Many portable devices are currently on the market are provided with applications which allow users to play games or interact with the interactive digital character such as virtual pets. In another example, there are various applications available in the digital marketplace which can be installed on the electronic device.

Most of the available virtual pet applications have only one goal—to grow and maintain a pet's happiness. This provides entertainment for a user initially, but they get bored quickly. In addition to that, over a period of time, once the virtual pet is fully grown, the user lost the interest in the application. Moreover, the present application doesn't take into the input of the present state of the user who is using the application.

SUMMARY

Embodiments of the present disclosure present technological improvements as solutions to one or more of the above-mentioned technical problems recognized by the inventors in conventional systems. For example, in one embodiment, a system for improving wellbeing of a person using a digital character is provided. The system comprises an electronic device. The electronic device comprises a display device, at least one memory and one or more hardware processors in communication with at least one memory. The display device displays a wellbeing meter for the person and a wellbeing meter for the digital character, wherein they are set at a base value. The one or more hardware processors is configured to perform the steps of: making the digital character to perform a set of activities on the electronic device, wherein the set of activities are derived from five categories of a PERMA model for wellbeing; providing the set of activities to be performed by the person in real life and on the electronic device, wherein each of the set of activities has a range of values associated thereof; calculating the value out of the range for each of the set of activities performed by the person, wherein the value is calculated depending on how successfully the activity is performed by the person; calculating an average of the calculated values for each of the set of activities a wellbeing index for the person; calculating a wellbeing index for the digital character depending on how successfully the set of activities are performed by the digital character; displaying the wellbeing Index of the person and the digital character on the wellbeing meters of the person and the digital character respectively on the display device; providing a set of questions by the digital character to the person depending on the wellbeing index of the person; providing an input by the person in response to the set of questions; and recommending a second set of activities based on the input to improve upon the wellbeing index of the person.

Another aspect the embodiment here provides a method for improving wellbeing of a person using a digital character. Initially a wellbeing meter of the person and a wellbeing meter of the digital character is set at a base value on an electronic device. In the next step the digital character is asked to perform a set of activities on the electronic device, wherein the set of activities are derived from five categories of a PERMA model for wellbeing. Further, the set of activities are provided to be performed by the person in real life and on the electronic device, wherein each of the set of activities has a range of values associated thereof. In the next step, via one or more hardware processor, a value out of the range for each of the set of activities performed by the person, wherein the value is calculated depending on how successfully the activity is performed by the person. Further, an average of the calculated values is calculated for each of the set of activities to determine a wellbeing index for the person. In the next step, a wellbeing index is calculated for the digital character depending on how successfully the set of activities are performed by the digital character. In the next step, the wellbeing Index of the person and the digital character is displayed on the wellbeing meters of the person and the digital character respectively. In the next step, a set of questions are provided by the digital character to the person depending on the wellbeing index of the person. An input is then provided by the person in response to the set of questions. And finally, a second set of activities Another aspect of the embodiment here provides one or more non-transitory machine readable information storage mediums comprising one or more instructions which when executed by one or more hardware processors cause improving wellbeing of a person using a digital character. Initially a wellbeing meter of the person and a wellbeing meter of the digital character is set at a base value on an electronic device. In the next step the digital character is asked to perform a set of activities on the electronic device, wherein the set of activities are derived from five categories of a PERMA model for wellbeing. Further, the set of activities are provided to be performed by the person in real life and on the electronic device, wherein each of the set of activities has a range of values associated thereof. In the next step, via one or more hardware processor, a value out of the range for each of the set of activities performed by the person, wherein the value is calculated depending on how successfully the activity is performed by the person. Further, an average of the calculated values is calculated for each of the set of activities to determine a wellbeing index for the person. In the next step, a wellbeing index is calculated for the digital character depending on how successfully the set of activities are performed by the digital character. In the next step, the wellbeing Index of the person and the digital character is displayed on the wellbeing meters of the person and the digital character respectively. In the next step, a set of questions are provided by the digital character to the person depending on the wellbeing index of the person. An input is then provided by the person in response to the set of questions. And finally, a second set of activities are recommended based on the input to improve upon the wellbeing index of the person.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Glossary—Terms Used in the Embodiments

The expression "digital character" or "digital pet" or "virtual pet" or "virtual character" in the context of the present disclosure refers to a digital character which is being used in the application running on the electronic device. This digital character is represented as a companion to the person using the application.

The expression "person" or "user" or "player" in the context of the present disclosure refers to the person who is using the application present on the electronic device. The system is configured to improve the wellbeing of the person.

Figure 1:
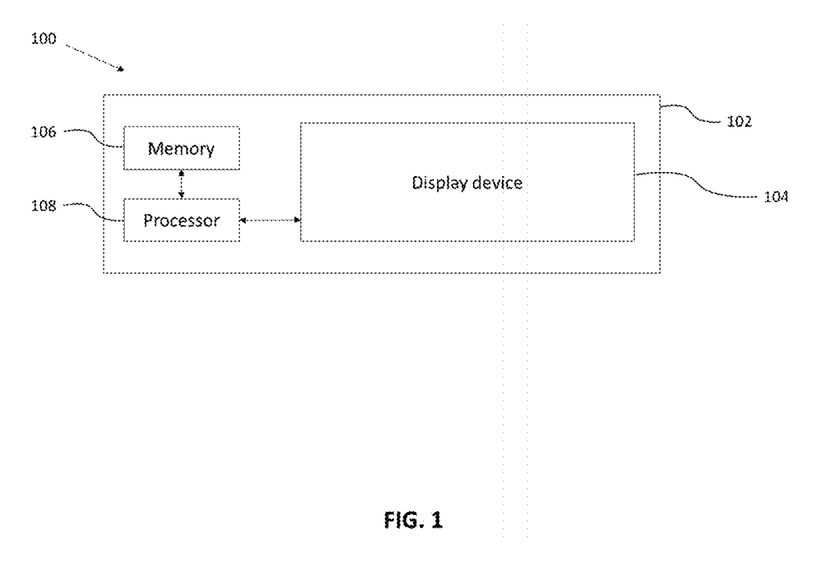
FIG. 1 illustrates a block diagram of a system for improving wellbeing of a person using a digital character according to an embodiment of the present disclosure.
Figure 2:
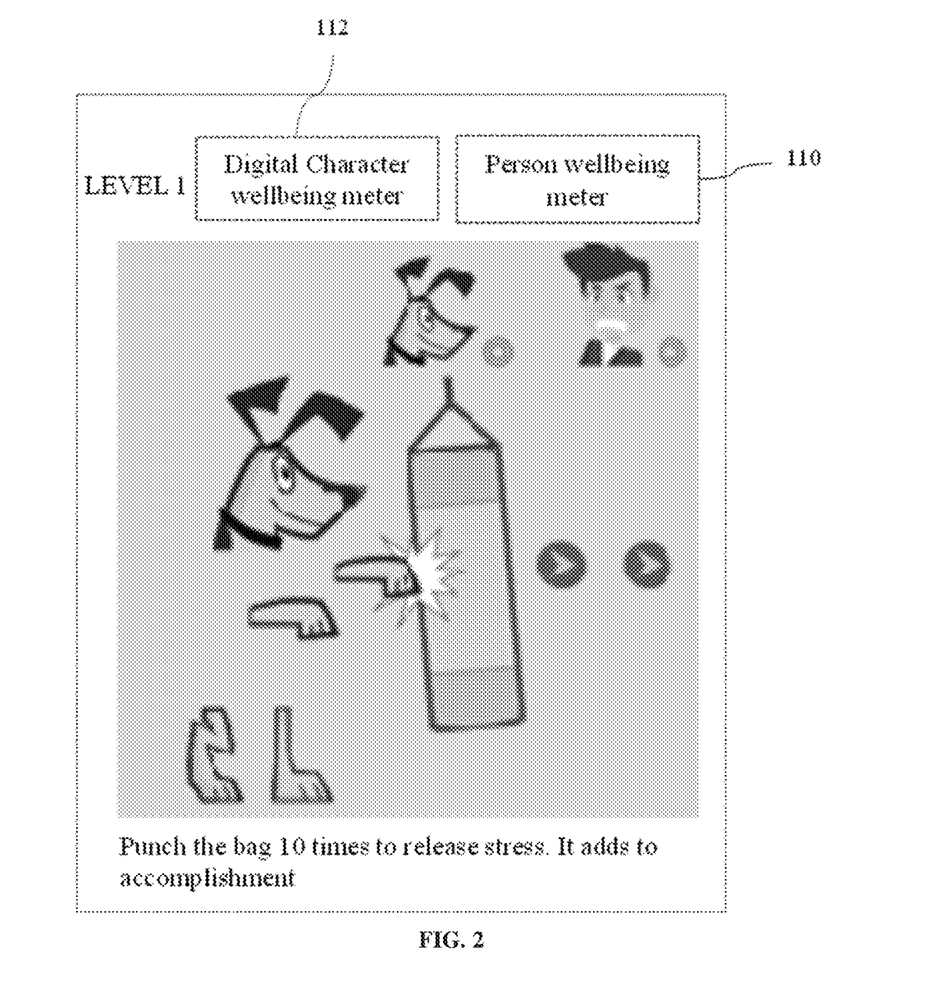
FIG. 2 shows a display device showing wellbeing meters and an example of an activity according to an embodiment of the present disclosure.
Figure 3A:
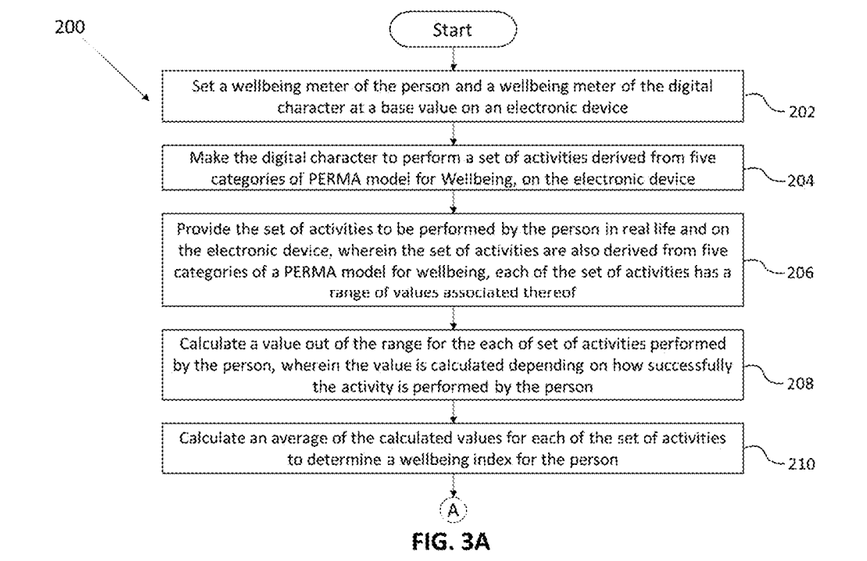
FIGS. 3A-3B is a flowchart illustrating the steps involved in improving wellbeing of a person using a digital character according to an embodiment of the present disclosure.
Figure 3B:
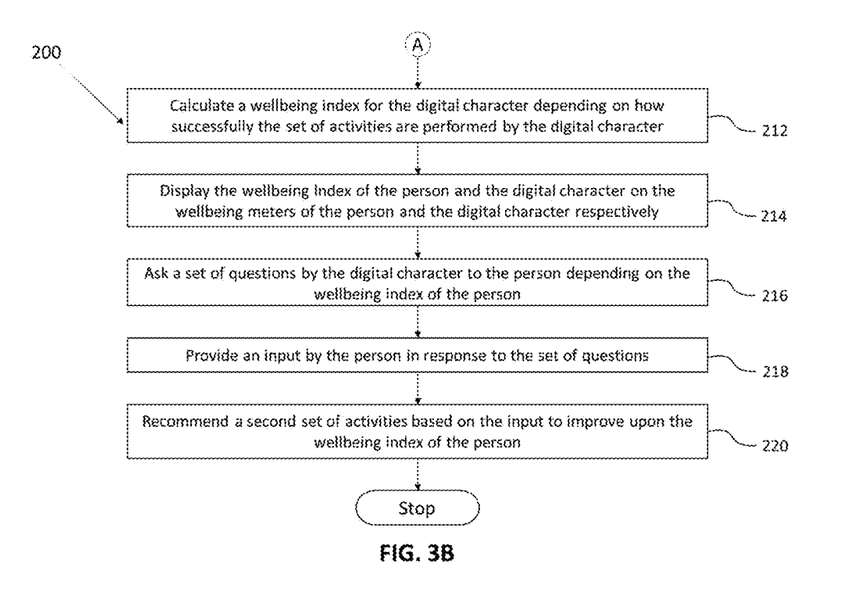

Referring now to the drawings, and more particularly to FIG. 1 through FIG. 3, where similar reference characters denote corresponding features consistently throughout the figures, there are shown preferred embodiments and these embodiments are described in the context of the following exemplary system and/or method.

According to an embodiment of the disclosure, a system 100 for improving wellbeing of a person using a digital character such as a digital pet is shown in the block diagram of FIG. 1. The system 100 comprises an application which can be installed on an electronic device 102 such as a mobile phone, a laptop, a computer or any other similar device. The wellbeing of the person or the user is measured using a wellbeing index. The system 100 is configured to improve the wellbeing index of the person by simultaneously indulging the person and the digital character in various activities. In addition to that the system 100 also configured to improve the wellbeing index of the digital character such as a digital pet. The system 100 is designed on the basis of a PERMA model of wellbeing.

According to an embodiment of the disclosure, the electronic device 102 further comprises a display device 104, a memory 106 and a processor 108 as shown in the block diagram of FIG. 1. The processor 108 works in communication with the memory 106. The processor 108 is configured to fetch the instruction from the memory as operated by the person. The processor 108 may further include a plurality of module for performing various function.

According to an embodiment of the disclosure, the system 100 is utilizing a digital character such as a digital pet or any other kind of a digital assistant. In an example the digital pet is a pet dog named as "TAPPY". The digital character is being provided as a companion to the person. The digital character is designed in such a way that it can understand moods of person/user and behave accordingly. The digital character is also made to patiently listen the conversations of the user and pretends to understand them and nods and acts accordingly. When the user is confused with some choices, the digital character also suggests to things that the user may like or the probable choice the user usually makes, for example by pointing his tail towards those choices or objects etc.

The digital character is designed with high IQ. The digital character is also very playful and active. The digital character is also capable to run and play in the park a lot. The digital character is also capable of performing various activities as explained in the later part of the disclosure. The digital character also requires attention from the user at a regular time interval. For example, the user may feed the digital character, converse with the digital character etc.

According to an embodiment of the disclosure, the display device 104 can also be used as a user interface. The display device 104 can be configured to take input from the person in the form of instruction which can be given to the digital character. The display device 104 can include a variety of software and hardware interfaces, for example, a web interface, a graphical user interface, and the likes and can facilitate multiple communications within a wide variety of networks N/W and protocol types, including wired networks, for example, LAN, cable, etc., and wireless networks, such as WLAN, cellular, or satellite.

According to an embodiment of the disclosure, the display device 104 further displays a person wellbeing meter 110 and a digital character wellbeing meter 112. A schematic representation of the display device 104 is shown in FIG. 2. The person wellbeing meter 110 is configured to display the wellbeing index ($W_P$) of the person. The digital character wellbeing meter 112 is configured to display the wellbeing index ($W_D$) of the digital character. It should be appreciated that the wellbeing meter for the person and the digital character can be set to a base value at the start of the application. It should be appreciated that the placement of the person wellbeing meter 110 and the digital character wellbeing meter 112 can be changed as per the requirement of the application designer.

According to an embodiment of the disclosure, the processor 108 is configured to provide a set of activities to be performed by the digital character on the electronic device 102. At the same time, the set of activities are also performed by the person in real life and using the electronic device 102. An example of activity is shown in FIG. 2, where the person is asked to operate the digital character to punch the bag 10 times to release stress. The set of activities are derived from five categories of a PERMA model for wellbeing. The PERMA Model for Wellbeing is designed by Martin Seligman. It involves a set of activities that will in some form involve or initiate five categories of the PERMA Model— Positive Emotions, Engagement, Relationships, Meaning and Accomplishments of the user. Each of the activities are has a range of values associated with them. A value can be chosen out of the range of values depending upon how successfully the person or the digital character completes that particular activity.

According to an embodiment of the disclosure, following are the five factors of the PERMA model which can be associated with the activities related to the digital character and the person as follows:

Positive emotion: Positive emotion involves feeding and inspecting the digital character. The inspecting may involve taking care. This may include one or more of following: Prepare and feed the digital character delicious foods and help the digital character grow, take care of yourself in the application as well as in your real life every day. For example, the digital character should be fed a minimum of three meals a day, the person should also be fed three meals a day.

Engagement: Engagement involves playing and spend time with the digital character every day. This may include one or more of following: Engage, interact, and play with the digital character for at least 15 minutes per day. Also person engaging in certain activities in real life will improve his Engagement factor.

Relationships: Relationships involves growing the person's relationship with the digital character and in the real life with other people. This may include one or more following: Making the person's relationship with the digital character better by increasing the conversations, sharing problems with the digital character which will in turn enable the digital character to prompt the person to take necessary actions in the real life of the person Meaning: Meaning involves helping the digital character achieve Quests. This may include one or more of following: Helping the digital character complete small quests by which enabling the digital character to prompt the person for real life Quests.

Accomplishment: Accomplishment involves helping the digital character achieve tangible Goals. This may include one or more of following: Helping the digital character complete tangible goals by which enabling the digital character to prompt the person to complete their real life goals.

In an example, for each of the factors, a behavior based actions list has been populated. Though this list can be modified in another example. For positive emotion may be initiated from music, warm baths, special foods, mindfulness—aware of your surroundings, meditation (guided meditation), Concentration etc. Engagement can be initiated from puzzle solving, hobbies, reading books. Relationships can be initiated from communication, calling the person's family, talk to neighbors, speak to caregivers, counsellors, attenders and self-efficacy—Asking for help is not bad and don't feel shy. Meaning can be initiated from self-worth, legacy, hope, optimism etc. Accomplishment can be initiated from puzzle solving goals, exercises: swimming, dancing, progressive challenges, basic food needs, basic cleanliness: brushing teeth, taking bath, fall prevention (risk of falls), motor disability etc.

According to an embodiment of the disclosure, the processor 108 is further configured to calculate the value for the each of set of activities performed by the person, wherein the value is calculated depending on how successfully the particular activity is performed by the person. The average for the calculated values is referred as the wellbeing index ($W_P$) for the person. Similarly, the processor 108 also calculates the wellbeing index ($W_D$) for the digital character depending on how successfully the activities are performed by the digital character. If the wellbeing index of the person and the digital character is low, it indicates the person and digital character are sad or upset.

According to an embodiment of the disclosure, the wellbeing index of the person and the digital character can be displayed on the wellbeing meters 110 and 112 of the person and the digital character respectively present on the display device 104. The wellbeing index is being updated dynamically. As soon as each of the activities are completed, the wellbeing index is updated accordingly in the wellbeing meters.

According to an embodiment of the disclosure, the processor 108 is further configured to ask a set of questions. The set of questions are provided by the digital character to the person depending on the wellbeing index of the person. The set of questions are designed according to the mood or feelings of the person deciphered from the wellbeing index of the person. Further, the processor 108 configured to receive an input by the person in response to the set of questions. The processor 108 is further configured to recommending a second set of activities based on the input to improve upon the wellbeing index of the person. The second set of activities are the next set of activities are chosen in such a way that the mood of the person be lifted up. For example, playing a fun game, watch a comedy movie etc.

According to an embodiment of the disclosure, the system 100 further requires an inspection of the digital character by the user after every predefined time interval. The inspection may involve basic activities of taking care like feeding the digital character, taking a walk with the digital character etc.

In operation, a flowchart 200 illustrating a method for improving wellbeing of a person using the digital character. Initially at step 202, the person's wellbeing meter the digital character's wellbeing meter is set at the base value on the electronic device 102. In the next step 204, the digital character is made to perform the set of activities on the electronic device 102. The application is designed in such a way that whenever the application starts the set of activities are performed by the digital character. At step 206, the set of activities are provided to be performed by the person in real life and on the electronic device 102. The set of activities are derived from five categories of the PERMA model for wellbeing, wherein each of the set of activities has a range of values associated thereof.

In the next step 208, a value out of the range of values for the each of set of activities performed by the person is calculated. The value is calculated depending on how successfully that particular activity is performed by the person. At step 210, the average is calculated for the calculated value for each of the set of activities to determine the wellbeing index for the person. Similarly, at step 212, the wellbeing index for the digital character is calculated depending on how successfully the set of activities are performed by the digital character. In the next step 214, the wellbeing Index of the person and the digital character is displayed on the wellbeing meters 110 and 112 of the person and the digital character respectively. The wellbeing meter is updated dynamically, as soon as one activity is completed, the person's and digital character's wellbeing meter is updated automatically.

In the next step 216, a set of questions are provided by the digital character to the person depending on the wellbeing index. For example, if the wellbeing index of the person is low means the person is sad and the set of questions will be provided in such a way that the mood of the person is further validated. In the next step 218, an input is provided by the person in response to the set of questions. And finally at step 220, a second set of activities or the next set of activities are recommended based on the provided input to improve upon the wellbeing index of the person. For example, if the person is sad, then the second set of activities may include watching a comedy movie or pursue any hobby etc.

According to an embodiment of the disclosure, the system 100 can also be provided with a write diary feature. Once write diary feature is selected by the person, the digital character will ask a question and he will take his digital diary (Tab) and his digital pen and starts to listen to the person, once the person starts talking. The digital character starts noting down the person's responses in his tab.

According to an embodiment of the disclosure, the system 100 can also be provided more than one level. As soon as the time passes by after the passing of time, the level of the application can be increased based on some predefined criteria.

According to an embodiment of the disclosure, the system 100 can also be described with the help of examples. In an example the application can work on two worlds. First one is the normal world: A simulation world where the digital character lives a regular life. Second is the fantasy world where all the adventures happen and the digital character tries to be successful in these adventures. The person/user starts in the simulation world and goes on the fantasy world to finish the quests whenever required and in turn improving the wellbeing index of himself and the digital character.

In the fantasy world, the user does game activities via the digital character and real life activities to enable the digital character to overcome dangerous situations and enemies. When the digital character gets tired in the fantasy world, person takes the digital character back to the normal world makes him perform normal activities to refill his meters and resumes the adventures in the fantasy world.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A method for improving wellbeing of a person using a digital character, the method comprising a processor implemented steps of:

setting, via one or more hardware processor, a wellbeing meter of the person and a wellbeing meter of the digital character at a base value on an electronic device;

making, via one or more hardware processor, the digital character to perform a set of activities on the electronic device whenever an application is invoked, wherein the set of activities are derived from five categories of positive emotion, engagement, relationship, meaning and accomplishment, a PERMA model for wellbeing, wherein the set of activities corresponding to the positive emotion involves feeding and inspecting the digital character, and the set of activities corresponding to the engagement involves interaction and playing with the digital character at least 15 minutes a day;

providing, via one or more hardware processor, the set of activities to be performed by the person in real life and on the electronic device, wherein each of the set of activities has a range of values associated thereof;

calculating, via one or more hardware processor, a value out of the range for the each of set of activities performed by the person, wherein the value is calculated depending on how successfully the activity is performed by the person;

calculating, via one or more hardware processor, an average of the calculated values for each of the set of activities to determine a wellbeing index for the person;

calculating, via one or more hardware processor, a wellbeing index for the digital character depending on how successfully the set of activities are performed by the digital character;

displaying, via one or more hardware processor, the wellbeing index of the person and the digital character on the wellbeing meters of the person and the digital character respectively, wherein the wellbeing index is dynamically updated;

providing, via one or more hardware processor, a set of questions by the digital character to the person depending on the wellbeing index of the person;

providing, via one or more hardware processor, an input by the person in response to the set of questions asked by the digital character, wherein the digital character patiently listens to conversations of the person and pretends to understand the conversations and nods, wherein the digital character suggests things that the person like or probable choice that the person usually make by pointing tail towards the choice or objects in a display device, wherein the display device is an user interface that takes input from the person in form of instructions and given to the digital character;

recommending, via one or more hardware processor, a second set of activities based on the input to improve upon the wellbeing index of the person; and inspecting the digital character by the person after every predefined time interval, wherein inspecting corresponds to activities of feeding the digital character, taking a walk with the digital character, wherein the application work on two worlds namely a simulation world and a fantasy world, wherein the person starts from the simulation world and enters a fantasy world, and in the fantasy world, the person plays game activities via the digital character.

2. The method of claim 1, wherein the digital character is a digital pet or a digital assistant.

3. The method of claim 1, wherein the set of questions provided by the digital character includes questions about the feelings of the person.

4. The method of claim 1, wherein the wellbeing index is measured based on the five categories of the PERMA model.

5. The method of claim 4, wherein the positive emotion is initiated for the person by feeding and inspecting the digital character a minimum of three meals a day and by feeding oneself in the real life three meals a day.

6. The method of claim 4, wherein the engagement is initiated for the person by playing and spending time with the digital character and by doing similar activities in the real life.

7. The method of claim 4, wherein the relationships are initiated for the person by nurturing the relationship with the digital character and nurturing similar relationships in the real life.

8. The method of claim 4, wherein the meaning is initiated for the person by helping the digital character achieve quests and by the person achieving similar quests in the real life.

9. The method of claim 4, wherein the accomplishments are initiated for the person by helping the digital character achieve tangible goals and by the person achieving similar tangible goals in the real life.

10. A system for improving wellbeing of a person using a digital character, the system comprises:
an electronic device, wherein the electronic device comprising:
a display device for displaying a wellbeing meter for the person and a wellbeing meter for the digital character, wherein they are set at a base value;
at least one memory; and
one or more hardware processors in communication with the at least one memory, wherein the one or more hardware processors is configured to perform the steps of:
making the digital character to perform a set of activities on the electronic device whenever an application is invoked, wherein the set of activities are derived from five categories of positive emotion, engagement, relationship, meaning and accomplishment, a PERMA model for wellbeing, wherein the set of activities corresponding to the positive emotion involves feeding and inspecting the digital character, and the set of activities corresponding to the engagement involves interaction and playing with the digital character at least 15 minutes a day;
providing the set of activities to be performed by the person in real life and on the electronic device, wherein each of the set of activities has a range of values associated thereof;
calculating the value out of the range for the each of set of activities performed by the person, wherein the value is calculated depending on how successfully the activity is performed by the person;
calculating an average of the calculated values for each of the set of activities a wellbeing index for the person;
calculating a wellbeing index for the digital character depending on how successfully the set of activities are performed by the digital character;
displaying the wellbeing Index of the person and the digital character on the wellbeing meters of the person and the digital character respectively on the display device, wherein the wellbeing index is dynamically updated;
providing a set of questions by the digital character to the person depending on the wellbeing index of the person;
providing an input by the person in response to the set of questions asked by the digital character, wherein the digital character patiently listens to conversations of the person and pretends to understand the conversations and nods, wherein the digital character suggests things that the person like or probable choice that the person usually make by pointing tail towards the choice or objects in a display device, wherein the display device is an user interface that takes input from the person in form of instructions and given to the digital character;
recommending a second set of activities based on the input to improve upon the wellbeing index of the person; and
inspecting the digital character by the person after every predefined time interval, wherein inspecting corresponds to activities of feeding the digital character, taking a walk with the digital character, wherein the application work on two worlds namely a simulation world and a fantasy world, wherein the person starts from the simulation world and enters a fantasy world, and in the fantasy world, the person plays game activities via the digital character.

11. One or more non-transitory machine readable information storage mediums comprising one or more instructions which when executed by one or more hardware processors cause managing a plurality of events, the instructions cause:
setting, via one or more hardware processor, a wellbeing meter of the person and a wellbeing meter of the digital character at a base value on an electronic device;
making, via one or more hardware processor, the digital character to perform a set of activities on the electronic device whenever an application is invoked, wherein the set of activities are derived from five categories of positive emotion, engagement, relationship, meaning and accomplishment, a PERMA model for wellbeing, wherein the set of activities corresponding to the positive emotion involves feeding and inspecting the digital character, and the set of activities corresponding to the engagement involves interaction and playing with the digital character at least 15 minutes a day;

providing, via one or more hardware processor, the set of activities to be performed by the person in real life and on the electronic device, wherein each of the set of activities has a range of values associated thereof;

calculating, via one or more hardware processor, a value out of the range for the each of set of activities performed by the person, wherein the value is calculated depending on how successfully the activity is performed by the person;

calculating, via one or more hardware processor, an average of the calculated values for each of the set of activities to determine a wellbeing index for the person;

calculating, via one or more hardware processor, a wellbeing index for the digital character depending on how successfully the set of activities are performed by the digital character;

displaying, via one or more hardware processor, the wellbeing Index of the person and the digital character on the wellbeing meters of the person and the digital character respectively, wherein the wellbeing index is dynamically updated;

providing, via one or more hardware processor, a set of questions by the digital character to the person depending on the wellbeing index of the person;

providing, via one or more hardware processor, an input by the person in response to the set of questions asked by the digital character, wherein the digital character patiently listens to conversations of the person and pretends to understand the conversations and nods, wherein the digital character suggests things that the person like or probable choice that the person usually make by pointing tail towards the choice or objects in a display device, wherein the display device is an user interface that takes input from the person in form of instructions and given to the digital character;

recommending, via one or more hardware processor, a second set of activities based on the input to improve upon the wellbeing index of the person; and inspecting the digital character by the person after every predefined time interval, wherein inspecting corresponds to activities of feeding the digital character, taking a walk with the digital character, wherein the application work on two worlds namely a simulation world and a fantasy world, wherein the person starts from the simulation world and enters a fantasy world, and in the fantasy world, the person plays game activities via the digital character.

* * * * *